United States Patent [19]

Wedemeyer et al.

[11] 4,358,616
[45] Nov. 9, 1982

[54] PROCESS FOR THE PREPARATION OF ALKYLTHIOMETHYLPHENOLS AND ARYLTHIOMETHYLPHENOLS

[75] Inventors: Karlfried Wedemeyer, Cologne; Helmut Fiege, Leverkusen, both of Fed. Rep. of Germany

[73] Assignee: Bayer Aktiengesellschaft, Leverkusen, Fed. Rep. of Germany

[21] Appl. No.: 211,987

[22] Filed: Dec. 1, 1980

Related U.S. Application Data

[63] Continuation of Ser. No. 65,687, Aug. 10, 1979, abandoned.

[30] Foreign Application Priority Data

Sep. 1, 1978 [DE] Fed. Rep. of Germany ....... 2838273

[51] Int. Cl.³ .......................................... C07C 148/00
[52] U.S. Cl. ...................................... 568/45; 568/44; 568/49; 568/50; 568/51; 568/52; 568/54
[58] Field of Search ...................... 568/44, 45, 49, 50, 568/51, 52, 54

[56] References Cited

U.S. PATENT DOCUMENTS

| 2,831,030 | 4/1958 | Chenicek | 568/45 |
| 3,179,701 | 4/1965 | Rocklin | 568/47 |
| 3,553,270 | 1/1971 | Wollensak et al. | 568/51 X |
| 3,903,173 | 9/1975 | Eggensperger et al. | 568/51 |
| 4,304,940 | 12/1981 | Wedemeyer et al. | 568/45 |

FOREIGN PATENT DOCUMENTS

| 1910588 | 9/1970 | Fed. Rep. of Germany . |
| 2614875 | 10/1977 | Fed. Rep. of Germany . |
| 1499043 | 1/1978 | United Kingdom | 568/51 |

OTHER PUBLICATIONS

Rudermann, et al., J. Am. Chem. Soc., 71(2), p. 264, (1949).
Poppelsdorf, et al., J. Chem. Soc. (1954), pp. 1124–1130.
Wagner, et al., "Lackunstharze", pp. 33–37, Munich, (1971).
Miyamoto, et al., Chemical Abstracts, 82, 86197x (1975).
Houben-Weyl, vol. 6/1C, 4th ed., p. 1042 (1976).

*Primary Examiner*—Robert Gerstl
*Assistant Examiner*—Diana G. Rivers
*Attorney, Agent, or Firm*—Felfe & Lynch

[57] ABSTRACT

The present invention provides a process for the preparation of an alkylthiomethylphenol or arylthiomethylphenol of the general formula

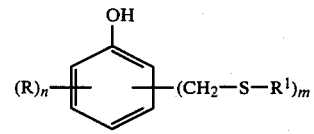

in which m, n, R and $R^1$ have the meaning mentioned in the specification, in which a hydroxymethylphenol of the general formula

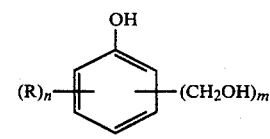

is reacted with a mercaptan or thiophenol at a temperature of from 20° to 200° C., if appropriate in the presence of a diluent.

29 Claims, No Drawings

PROCESS FOR THE PREPARATION OF ALKYLTHIOMETHYLPHENOLS AND ARYLTHIOMETHYLPHENOLS

This is a continuation of application Ser. No. 65,687, filed Aug. 10, 1979, now abandoned.

This invention relates to a process for the preparation of certain thiomethylphenol compounds, viz., alkylthiomethylphenols and arylthiomethylphenols.

Such compounds are useful as intermediates for the preparation of plant protection agents.

It is known that, for example, ethylthiomethylphenol can be obtained by reacting 2-chloromethylphenol with ethylmercaptan at 0°-10° C. in acetonitrile as the solvent. However, the yield is only 50% of theory and an equimolar amount of sodium methylate is required as the auxiliary base (German Patent Specification No. 1,910,588). Furthermore, the starting material, 2-chloromethylphenol, is industrially obtainable only with difficulty, firstly because its preparation by chloromethylation of phenol takes place unsatisfactorily and secondly because during its preparation—as with all chloromethylation reactions—the formation of chloromethyl ethers, which are known to be strongly carcinogenic, must be expected [see Houben-Weyl, Volume 6/1c, page 1,042, 4th edition (1976)].

In order to circumvent these difficulties, methylphenols, whose OH group is first protected by esterification, are used as starting materials. The methyl group of the phenol which has thus been protected is then converted by chlorination into the chloromethyl group, the latter is then reacted with an alkali metal mercaptide to give the alkylthiomethyl group, and thereafter the alkylthiomethylphenol is liberated by alkaline saponification of the ester group [Japanese Application 74/20,191; C.A. 82, 82,197x(1975)]. The process thus entails four reaction steps which cause substantial losses and are industrially rather unattractive.

Further, it is known that 4-methyl-2,6-bis-butylthiomethylphenol is obtained by reaction of (1 mol) of 4-methyl-2,6-bis-hydroxymethylphenol with (10 mol) of N-butylmercaptan in (25 mol) of glacial acetic acid. It is stated that preconditions for this reaction to take place are that the starting materials should be anhydrous, and that anhydrous hydrogen chloride or boron trifluoride should be present (I. W. Ruderman and E. M. Fettes, J. Am. Chem. Soc. 71 (1949), 2,264).

Apart from the moderate yield (60% of theory), the long reaction time (about 2 days) and the industrially rather diadvantageous conditions (anhydrous starting materials, use of HCl or BF$_3$, which in conjunction with the water of reaction give a very corrosive reaction mixture, poor space/time yields, and the expensive regeneration and dehydration of the materials acetic acid and mercaptan, which are employed in very large excess), an important disadvantage of the process is that it is restricted to hydroxymethylphenols in which the o- and/or p-positions relative to the phenolic OH group are no longer reactive (that is to say are substituted).

It is furthermore known that arylthiomethylnaphthols or alkylthiomethylnaphthols are obtained in є Mannich reaction, for example by reaction of β-naphthol with formaldehyde and arylmercaptan or alkylmercaptan (see F. Poppelsdorf and S. J. Holt, J. Chem. Soc. 1954, 1,124 et seq.). However, the reaction will only occur if triethylamine is simultaneously present as an auxiliary base, and even then requires reaction times of about 6 days to achieve satisfactory yields.

If this reaction is applied to phenol, the reaction product formed is not a single compound but a mixture of isomers, homoloques and resins (see U.S. Pat. No. 2,322,376, 1943).

It is also known that alkylthiomethyl-phenol mixtures are obtained by reaction of dialkylaminomethylphenols with alkylmercaptans (see U.S. Pat. No. 2,417,118, 1947). In this case, evidently the dialkylaminophenol, or the dialkylamine formed as a co-product during the reaction, serves as the auxiliary base.

The aforesaid process also has substantial technical disadvantages; for example, mixtures of isomeric and homologous alkylthiomethylphenols are formed in the process. Furthermore, the reaction times are 35-60 hours. This entails additional losses of yield owing to resinification, since the dialkylaminomethylphenols which serve as the starting compounds are not heat-stable at the required reaction temperatures and in part resinify during the long reaction time.

It is furthermore known that alkylthiomethylphenols and arylthiomethylphenols can be obtained by reaction of dialkylaminomethylphenols with thiocarboxylic acid S-alkyl and S-aryl esters respectively (see DE-AS (German Published Specification) No. 2,614,875, 1976).

This process has the disadvantage that the thiocarboxylic acid S-esters to be employed in the reaction are relatively valuable reaction components, compared to the mercaptan, and must first be prepared in a preceding reaction step from the mercaptan and a carboxylic acid halide. A further disadvantage of the process is that the dialkylamino component of the dialkylaminomethylphenol employed is lost as carboxylic acid dialkylamide. The latter is obtained, in the process, as a co-product in a contaminated form, and must be burnt or be worked up by expensive methods. Accordingly, the process entails the wastage of valuable chemicals, or entails high costs.

Thus, no process is as yet known which makes it possible satisfactorily to prepare alkylthiomethylphenols or arylthiomethylphenols without substantial technical effort and expenditure on auxiliary chemicals.

The present invention now provides a process for the preparation of an alkylthiomethylphenol or arylthiomethylphenol of the general formula

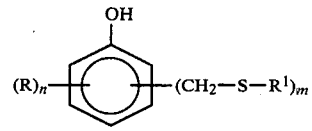

in which
  m represents 1, 2 or 3,
  n represents the number resulting from the difference (5-m) and
  each R, independently of any other R, represents hydrogen, alkyl, cycloalkyl, aryl, aralkyl, alkoxy, cycloalkoxy, aryloxy, halogen or nitro, or the R's represent a benzene ring or cycloalkane ring fused to the phenyl ring, and
  R$^1$ represents optionally substituted alkyl with 1 to 12 C atoms or represents cycloalkyl, optionally substituted phenyl or optionally substituted aralkyl,
in which a hydroxymethylphenol of the general formula

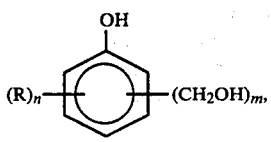

(II)

in which R, m and n have the above-mentioned meanings, is reacted with a mercaptan or thiophenol of the general formula

in which $R^1$ has the above-mentioned meaning, at a temperature of from 20° to 200° C., if appropriate in the presence of a diluent.

It must be described as distinctly surprising that in the process according to the invention alkylthiomethylphenols or arylthiomethylphenols are formed in good yields. According to the prior art extensive resinification was to be expected under the conditions according to the invention, especially in the case of hydroxymethylphenols having free ortho- and/or para-positions, since it is known that hydroxymethylphenols occur as thermally and chemically extremely labile intermediate stages in the manufacture of phenol-formaldehyde resin (compare H. Wagner and H. F. Sarx, Lackkunstharze (Synthetic Resins for Lacquers), Carl Hanser Verlag, Munich 1971, pages 35–36). Further, it was to be expected that the reaction of the mercaptan with the hydroxymethyl group would require the addition of strongly acid or strongly basic auxiliary materials (catalysts), which would in turn promote the tendency towards resinification.

The process according to the invention exhibits a number of advantages. Thus, it is unnecessary to use auxiliary materials and catalysts. The only co-product formed is water, which can be separated off easily, for example by distillation. The mercaptans can be employed directly in the reaction and do not first have to be converted to another compound. The starting materials do not have to be anhydrous. No particular corrosion problems arise. By selecting an appropriately high temperature, short reaction times, and hence high space/time yields, can be achieved. By using an appropriate diluent, the reaction can also be carried out at atmosphere pressure. The reaction parameters can be freely selected within wide limits and can therefore readily be adapted to industrial conditions.

When using 2-hydroxymethyl-phenol and ethylmercaptan as starting compounds, the course of the reaction can be represented by the following equation:

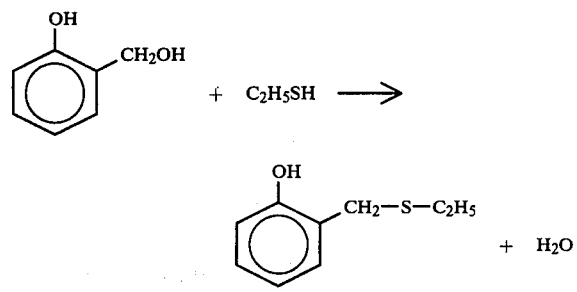

The formula (II) provides a general definition of the hydroxymethylphenols to be used according to the invention, as starting materials. In this formula, each R, independently of any other R, preferably represents hydrogen, alkyl with 1 to 6 C atoms, cycloalkyl with 3 to 6 C atoms, phenyl, benzyl or halogen (especially chlorine).

Hydroxymethylphenols of the formula (II) are in themselves known or can be prepared in accordance with known methods, for example by addition of formaldehyde to phenols (see J. F. Walker, "Formaldehyde", Reinhold, New York, 3rd edition, 1964, page 310 et seq.) or by reduction of phenolaldehydes.

The formula (III) provides a general definition of the mercaptans to be used, according to the invention, as starting materials. In this formula, $R^1$ preferably represents alkyl with 1 to 12 C atoms or alkoxy-substituted alkyl, cycloalkyl with 3 to 6 C atoms, phenyl, benzyl or alkyl-substituted and/or halogen-substituted phenyl.

Mercaptans of the formula (III) are in themselves known or can be prepared analogously to known processes.

In carrying out the process according to the invention, the amount of mercaptan to be employed per mole of hydroxymethyl group to be converted in the hydroxymethylphenol can vary within wide limits. Usually, amounts of about 1 mole of mercaptan per mole of hydroxymethyl group suffice. Since the mercaptan can at the same time also serve as a diluent, there are no upper limits to the mercaptan/hydroxymethylphenol ratio.

In the process according to the invention, it is possible to use as the diluent, not only the mercaptan in question, but also any desired inert protic or aprotic solvent.

The diluents used will preferably be water; aliphatic, cycloaliphatic and aromatic hydrocarbons (which can also be chlorinated), for example petrols, petroleum ether, toluene, xylene, chlorobenzene, cyclohexane, methylcyclohexane, tetralin and decalin; alcohols, for example methanol, ethanol, isopropanol, butanol, cyclohexanol, methylcyclohexanol and ethylene glycol; ethers, for example diethyl ether, diisopropyl ether, di-n-butyl ether, dioxan, tetrahydrofuran and diglyme; ether-alcohols, for example methylglycol, ethylglycol, butylglycol, methyldiglycol and ethyldiglycol; phenols for example phenol, cresol, xylenol and the phenol on which the particular hydroxymethylphenol is based; ketones, for example acetone, methyl ethyl ketone, methyl isobutyl ketone and cyclohexanone; carboxylic acid derivatives, for example dimethylformamide, dimethylacetamide and N-methylpyrrolidone; nitriles, for example acetonitrile or propionitrile; other nitrogen-containing organic solvents, for example pyridine, picoline and lutidine; sulphur-containing organic compounds, for example dimethylsulphoxide; or the reaction mixture formed according to the invention. Mixtures of these diluents can also be used.

The use of a diluent is not mandatory. Essentially, a diluent is used for technical reasons concerning the reaction, for example to ensure better mixing, better heat exchange and safe conduct of the reaction. Accordingly, the ratio of diluent to hydroxymethylphenol can be freely selected within wide limits. Weight ratios of diluent to hydroxymethylphenol of 1:1 to 20:1 are preferred. It is not necessary that all the starting materials and/or reaction products should dissolve completely in the diluent, that is to say the starting mixture and/or the reaction mixture can also be poly-phase systems. This can even be of advantage for working up the reaction product. For example, when carrying out the reaction in water as the diluent, a two-phase reaction mixture is formed, which can be separated, by simple phase separation, into the alkylthiomethylphenol or arylthiomethylphenol and an aqueous phase. The latter can (after taking off an amount corresponding to the water of reaction) be directly recycled to the next batch; accordingly, it does not have to be removed by distillation.

The process according to the invention can be carried out within a wide temperature range; in general, the reaction is carried out at a temperature of from 20° to 200° C., preferably at from 50° to 180° C.

The reaction can be carried out under normal pressure, for example also under reflux, or under autogenous pressure in an autoclave. The method of working depends on the vapour pressure of the reaction mixture, the technical circumstances and the desired reaction time. Working under autogenous pressure in an autoclave permits higher reaction temperatures and hence shorter reaction times. The method of working in an autoclave can be advantageous in the case of low-boiling mercaptans and low-boiling solvents or diluents. High-boiling solvents and diluents permit working at higher temperatures even under normal pressure.

It is not necessary, for the process according to the invention, that the hydroxymethylphenols (II) should, before being reacted according to the invention with the mercaptans (III), be present in the isolated (free) form. It is a great advantage of the process that the hydroxymethylphenol need not first be isolated in the free form, and instead its reaction with the mercaptan can, if desired, be carried out in the actual medium in which the hydroxymethylphenol is obtained during its preparation or isolation. For example, the hydroxymethylphenol can be prepared by reaction of formaldehyde in excess phenol, and the mercaptan can then be added to this reaction mixture in order to carry out the reaction according to the invention, to give the thiomethylphenol (I). In this case, the phenol on which the hydroxymethylphenol is based, and which is added in excess, serves as the diluent. This dispenses with the isolation of the hydroxymethylphenol and the reaction virtually amounts to a one-vessel reaction between formaldehyde, the phenol and the mercaptan.

The same situation applies if, for example, a suitable phenolaldehyde is dissolved in an alcohol, the phenolaldehyde is reduced to the hydroxymethylphenol (with Raney nickel) and subsequently (if necessary after separating off the catalyst) the mercaptan is added to the reaction mixture and the reaction according to the invention, to give the thiomethylphenol (I), is carried out.

The alkylthiomethylphenol or arylthiomethylphenol formed is isolated by separation from the diluents in accordance with the known methods. In the reaction according to the invention, the diluent can be reused. By-products can, where necessary, be removed entirely or partially in accordance with conventional processes. The water formed as a by-product can even be removed whilst the reaction is proceeding.

The alkylthiomethylphenols and arylthiomethylphenols which can be prepared by the process according to the invention can be used as intermediates for the synthesis of plant protection agents, especially insecticidal active compounds such as 2-(ethylthiomethylphenyl)-N-methyl-carbamate (see German Patent Specification No. 1,910,588 and DE-OS (German Published Specification) No. 2,122,311).

The process of the present invention is illustrated by the following preparative Examples.

EXAMPLE 1

A mixture of 99.2 g (0.8 mol) of 2-hydroxymethylphenol and 124 g (2 mol) of ethylmercaptan was heated for 5 hours to 170° C. in a VA autoclave, whilst stirring. After cooling to room temperature, the unconverted ethylmercaptan and the water of reaction were distilled off under normal pressure, and subsequently the 2-ethylthiomethyl-phenol was distilled off under 1.5 mm Hg. 128 g of 2-ethylthiomethyl-phenol (ca. 95% of theory) were obtained.

EXAMPLE 2

A mixture of 49.6 g (0.4 mol) of 2-hydroxymethylphenol and 124 g (2 mol) of ethylmercaptan was heated for 5 hours to 170° C. in a stirred autoclave. Working up as in Example 1 gave 32.2 g (96% of theory) of 2-ethylthiomethyl-phenol.

EXAMPLE 3

A mixture of 24.8 g of 2-hydroxymethyl-phenol, 124 g of ethylmercaptan and 40 g of methanol was heated for 5 hours to 140° C. in a stirred autoclave, cooled and worked up by distillation. Yield 31.3 g (93% of theory) of 2-ethylthiomethyl-phenol.

EXAMPLE 4

A mixture of 49.6 g (0.4 mol) of 2-hydroxymethylphenol, 24.8 g (0.4 mol) of ethylmercaptan and 90 g of diisopropyl ether was heated for 5 hours to 170° C. in a VA stirred autoclave. After cooling, the water of reaction and solvent were first distilled off under normal pressure, after which the 2-ethylthiomethyl-phenol was distilled off under <2 mm Hg. Yield: 60.5 g of 2-ethylthiomethyl-phenol (ca. 90% of theory).

EXAMPLE 5

A mixture of 49.6 g (0.4 mol) of 2-hydroxymethylphenol, 180 g of diisopropyl ether and 29.8 g (0.48 mol) of ethylmercaptan was heated for 5 hours at 170° C. in a VA autoclave, under autogenous pressure, cooled and worked up as in Example 1. Yield of 2-ethylthiomethylphenol: 95% of theory, relative to 2-hydroxymethylphenol.

EXAMPLE 6

A mixture of 450 g of phenol, 0.8 g of zinc acetate and 24 g of paraformaldehyde was warmed for 6 hours to 70° C. in a flask equipped with a stirrer and a reflux condenser. 49.6 g of ethylmercaptan were then added to the reaction mixture and the reaction temperature in the flask was raised progressively so that there was always a slight reflux. After about 12 hours, when a final temperature of 120° C. had been reached, the reaction was stopped by cooling and the reaction mixture was worked up by distillation. The phenol could be re-used in a subsequent reaction. The yield of isolated 2-ethylthiomethyl-phenol was 70% of theory, relative to paraformaldehyde, and about 95%, relative to the 2-hydroxymethyl-phenol formed as an intermediate.

EXAMPLE 7

A mixture of 49.6 g (0.4 mol) of 2-hydroxymethylphenol, 24.8 g (0.4 mol) of ethylmercaptan and 200 ml of o-dichlorobenzene was heated in a flask equipped with a stirrer and a reflux condenser, under normal pressure, and starting from room temperature, in such a way that there was always a moderate reflux and that the final temperature in the flask did not exceed about 125° C. In total, the mixture was heated under reflux for about 20 hours. Thereafter, working up by distillation gave 2-ethylthiomethyl-phenol in a yield of 87% of theory. The o-dichlorobenzene distilled off could be re-used in a subsequent batch.

EXAMPLE 8

A mixture of 62 g (0.5 mol) of 4-hydroxymethyl-phenol, 37 g (0.6 mol) of ethylmercaptan and 230 g of phenol was first heated, in a flask equipped with stirrer and reflux condenser, under normal pressure to about 85° C. in the course of about 15 minutes, and was then heated further in such a way that there was always a moderate reflux and that ultimately a final temperature of about 130° C. in the flask was reached. After a reaction time of 18 hours at 85°–130° C., the mixture was cooled and worked up by distillation. 4-Ethylthiomethyl-phenol was obtained in a yield of 65% of theory.

EXAMPLES 9 to 18

49.6 g (0.4 mol) of 2-hydroxymethyl-phenol were reacted with 24.8 g (0.4 mol) of ethylmercaptan in 200 ml of solvent or diluent for 5 hours at 170° C. under autogenous pressure in a VA stirred autoclave. Depending on the solvent or diluent, working up by distillation gave the following yields of 2-ethylthiomethyl-phenol (Table 1):

TABLE 1

| Example No. | Solvent or diluent | 2-Ethylthiomethyl-phenol Yield, % of theory |
| --- | --- | --- |
| 9 | Cyclohexane | 91 |
| 10 | Toluene | 95 |
| 11 | o-Xylene | 91 |
| 12 | Chlorobenzene | 87 |
| 13 | Isopropanol | 90 |
| 14 | Glycol monomethyl ether (methylglycol) | 95 |
| 15 | Pyridine | 91 |
| 16 | Acetonitrile | 89 |
| 17 | Dimethylformamide | 86 |
| 18 | Water | 73(+) |

(+)The reaction mixture consisted of an aqueous phase and 63 g of an organic phase. The distillation of the organic phase gave the above yield.

EXAMPLES 19 to 24

49.6 g (0.4 mol) of 2-hydroxymethyl-phenol were heated with 0.4 mol of a mercaptan (see Table 2) in the presence of 200 ml of diisopropyl ether for 5 hours to 170° C. under autogenous pressure in a VA autoclave. After cooling to room temperature, the mixture was worked up in accordance with conventional procedures. The 2-alkylthiomethyl-phenol and 2-arylthiomethyl-phenols obtained in accordance with the mercaptan employed, and their yields, are summarised in Table 2:

TABLE 2

| Example No. | Mercaptan | 2-Alkylthiomethyl-phenol or 2-Arylthiomethyl-phenol | % of theory |
| --- | --- | --- | --- |
| 19 | Methylmercaptan | 2-Methylthiomethylphenol | 93 |
| 20 | Isopropylmercaptan | 2-Isopropylthiomethyl-phenol | 88 |
| 21 | n-Butylmercaptan | 2-n-Butylthiomethylphenol | 84 |
| 22 | Benzylmercaptan | 2-Benzylthiomethylphenol | 90 |
| 23 | Thiophenol | 2-Phenylthiomethylphenol | 91 |

TABLE 2-continued

| Example No. | Mercaptan | 2-Alkylthiomethyl-phenol or 2-Arylthiomethyl-phenol | % of theory |
| --- | --- | --- | --- |
| 24 | 4-Chlorothiophenol | 2-(4-Chloro-phenyl)-thio-methyl-phenol | 70(+) |

(+)Heated for 10 hours to 170° C. under autogenous pressure.

EXAMPLES 25 to 28

0.4 mol of hydroxymethylphenol in 200 ml of diisopropyl ether were reacted with 0.4 mol of ethylmercaptan per mol of hydroxymethyl group for 5 hours at 170° C. in a stirred autoclave. After cooling to room temperature, the mixture was worked up in accordance with conventional procedures. The ethylthiomethylphenols obtained in accordance with the hydroxymethylphenol employed, and their yields, are summarised in Table 3.

TABLE 3

| Example No. | Hydroxymethylphenol | Ethylthiomethylphenol | % of theory |
| --- | --- | --- | --- |
| 25 | 4-Methyl-2-hydroxymethyl-phenol | 4-Methyl-2-ethylthiomethyl-phenol | 91 |
| 26 | 4-Chloro-6-methyl-2-hydroxymethyl-phenol | 4-Chloro-6-methyl-2-ethylthiomethyl-phenol | 95 |
| 27 | 4,6-Dichloro-2-hydroxymethyl-phenol | 4,6-Dichloro-2-ethylthiomethyl-phenol | 70 |
| 28 | 4-Methyl-2,6-bis-(hydroxymethyl)phenol | 4-Methyl-2,6-bis-(ethylthiomethyl)-phenol | 94 |

It will be understood that the specification and examples are illustrative but not limitative of the present invention and that other embodiments within the spirit and scope of the invention will suggest themselves to those skilled in the art.

What is claimed:

1. Process for the preparation of a thio-methylphenol compound of the formula

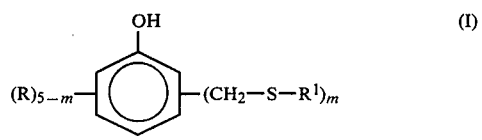

wherein
  m is 1, 2 or 3; each R is individually selected from hydrogen, alkyl, cycloalkyl, aryl, aralkyl, alkoxy, cycloalkoxy, aryloxy, halogen or nitro; or the R's taken together represent a benzene ring or a cycloalkane ring fused to the phenyl ring of formula (I); and
  $R^1$ is alkyl of 1–12 carbon atoms, alkoxy-substituted alkyl of 1–12 carbon atoms, cycloalkyl; phenyl; halogen-substituted phenyl; or aralkyl,
which process comprises, in the absence of a catalyst, reacting an hydroxymethylphenol of the formula

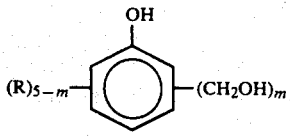

wherein

R and m are defined as above with a mercaptan or thiophenol of the formula $$R^1\text{—S—H}$$

where
$R^1$ is defined as above, at a temperature from 50° C. to 200° C.

2. Process as claimed in claim 1 wherein the process carried out in the presence of a diluent.

3. Process as claimed in claim 1 wherein the process is carried out at a temperature of up to 180° C.

4. Process as claimed in claim 1 wherein the reaction is effected in the presence of a diluent selected from at least one member of the group consisting of water, an aliphatic aromatic or cycloaliphatic hydrocarbon, which may be chlorinated, an alcohol, an ether, an ether-alcohol, a phenol, a ketone, an amide, a nitrile or a mixture of any of these diluents.

5. Process as claimed in claim 1 wherein an excess of the mercaptan (III) is employed as the diluent.

6. Process as claimed in claim 1 wherein a weight ratio of diluent to hydroxymethylphenol of 1:1 to 20:1 is employed.

7. Process as claimed in claim 1–6 wherein the hydroxymethylphenol of formula (II) is prepared in situ.

8. Process as claimed in claim 1 wherein m is 1.
9. Process as claimed in claim 1 wherein m is 2.
10. Process as claimed in claim 1 wherein m is 3.
11. Process as claimed in claim 1 wherein R is hydrogen.
12. Process as claimed in claim 1 wherein R is alkyl.
13. Process as claimed in claim 1 wherein R is cycloalkyl.
14. Process as claimed in claim 1 wherein R is aryl.
15. Process as claimed in claim 1 wherein R is aralkyl.
16. Process as claimed in claim 1 wherein R is alkoxy.
17. Process as claimed in claim 1 wherein R is cycloalkoxy.
18. Process as claimed in claim 1 wherein R is aryloxy.
19. Process as claimed in claim 1 wherein R is halogen or nitro.
20. Process as claimed in claim 1 wherein the R's taken together represent a benzene ring.
21. Process as claimed in claim 1 wherein the R's taken together represent a cycloalkane ring.
22. Process as claimed in claim 1 wherein $R^1$ is alkyl or alkoxy substituted alkyl.
23. Process as claimed in claim 1 wherein $R^1$ is cycloalkyl.
24. Process as claimed in claim 1 wherein $R^1$ is phenyl or halogen substituted phenyl.
25. Process as claimed in claim 1 wherein $R^1$ is aralkyl.
26. Process for the preparation of a thiomethylphenol compound of the formula

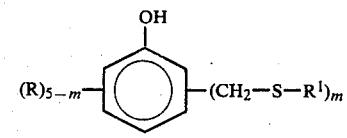

wherein
m is 1, 2 or 3;
each R is individually selected from hydrogen, cycloalkyl, aryl, aralkyl, alkoxy, cycloalkoxy, aryloxy, halogen or nitro; or the
R's taken together represent a benzene ring or a cycloalkane ring fused to the phenyl ring of formula (I); and
$R^1$ is halogen substituted phenyl;
which process comprises
in the absence of a catalyst, reacting an hydromethylphenol of the formula

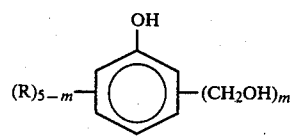

wherein
R and m are defined as above with a mercaptan or thiophenol of the formula $$R^1\text{—S—H} \quad (III)$$

wherein
$R^1$ is defined as above, at a temperature from 20° to 200° C.

27. Process as claimed in claim 26, wherein the reaction is effected in the presence of a diluent selected from at least one member of the group consisting of water, an aliphatic, aromatic or cycloaliphatic hydrocarbon, which may be chlorinated, an alcohol, an ether, an ether-alcohol, a phenol, a ketone, an amide, a nitrile or a mixture of any of these diluents.

28. Process as claimed in claim 26 where the hydroxymethylphenol of the formula (II) is further defined by having at least one of the ortho or para-positions to the hydroxyl be hydrogen.

29. Process as claimed in claim 1 wherein the hydroxymethylphenol of the formula (II) is further defined by having at least one of the ortho- or para-positions to the hydroxyl be hydrogen.

* * * * *